US008418439B2

(12) United States Patent
Ding (10) Patent No.: US 8,418,439 B2
(45) Date of Patent: Apr. 16, 2013

(54) NO$_x$ SENSOR AMBIENT TEMPERATURE COMPENSATION (75) Inventor: Yi Ding, Canton, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 909 days.

(21) Appl. No.: 12/388,010

(22) Filed: Feb. 18, 2009

(65) Prior Publication Data
US 2010/0205938 A1 Aug. 19, 2010

(51) Int. Cl.
F01N 3/00 (2006.01)

(52) U.S. Cl.
USPC .................................. 60/286; 60/277; 60/287

(58) Field of Classification Search .............. 60/276, 60/284, 285, 301, 277, 286; 204/781, 424, 204/425, 426; 219/202, 205
See application file for complete search history.

(56) References Cited

U.S. PATENT DOCUMENTS

| | | | | |
|---|---|---|---|---|
| 5,291,673 A * | 3/1994 | Hamburg et al. | | 60/274 |
| 6,083,370 A | 7/2000 | Kato et al. | | |
| 6,120,677 A | 9/2000 | Yamada et al. | | |
| 6,214,207 B1 * | 4/2001 | Miyata et al. | | 205/781 |
| 6,228,252 B1 | 5/2001 | Miyata et al. | | |
| 6,254,765 B1 | 7/2001 | Diehl | | |
| 6,309,536 B1 * | 10/2001 | Inagaki et al. | | 205/781 |
| 6,311,480 B1 * | 11/2001 | Suzuki et al. | | 60/276 |
| 6,332,965 B1 | 12/2001 | Sugiyama et al. | | |
| 6,348,140 B1 * | 2/2002 | Matsubara et al. | | 204/424 |
| 6,578,563 B2 * | 6/2003 | Hada et al. | | 123/697 |
| 6,586,711 B2 * | 7/2003 | Whitney et al. | | 219/497 |
| 6,720,534 B2 | 4/2004 | Hada et al. | | |
| 7,017,567 B2 * | 3/2006 | Hosoya et al. | | 123/697 |
| 7,900,614 B2 * | 3/2011 | Ding | | 123/672 |
| 2001/0000598 A1 * | 5/2001 | Miyata et al. | | 205/780.5 |
| 2002/0000436 A1 * | 1/2002 | Hashimoto et al. | | 219/497 |
| 2002/0179594 A1 * | 12/2002 | Hada et al. | | 219/494 |
| 2005/0029250 A1 * | 2/2005 | Niwa et al. | | 219/494 |
| 2008/0110769 A1 * | 5/2008 | Wang et al. | | 205/781 |
| 2009/0038595 A1 * | 2/2009 | Arlt et al. | | 123/676 |
| 2009/0114536 A1 * | 5/2009 | Ishiguro et al. | | 204/406 |
| 2009/0139212 A1 * | 6/2009 | Miwa | | 60/277 |
| 2011/0023459 A1 * | 2/2011 | Nieuwstadt et al. | | 60/285 |

FOREIGN PATENT DOCUMENTS
WO WO 2007099013 A1 * 9/2007

* cited by examiner

Primary Examiner — Thomas Denion
Assistant Examiner — Patrick Maines
(74) Attorney, Agent, or Firm — Julia Voutyras; Alleman Hall McCoy Russell & Tuttle LLP (57) ABSTRACT Various systems and methods are described for controlling an engine in a vehicle during engine operation, the engine having an exhaust and a NO$_x$ sensor coupled in the engine exhaust, in response to an ambient temperature of the NO$_x$ sensor. One example method comprises, during warm-up of the NO$_x$ sensor and during cold engine starting, adjusting an engine operating condition in response to a NO$_x$-indicative reading of the NO$_x$ sensor, the NO$_x$-indicative reading being compensated for ambient temperature effects on the NO$_x$ sensor.

20 Claims, 6 Drawing Sheets

United States Patent US 8,418,439 B2

NO$_x$ SENSOR AMBIENT TEMPERATURE COMPENSATION

TECHNICAL FIELD

The present application relates to a gas sensor for measuring emissions from motor vehicles, and more particularly, for measuring nitrogen oxide (NO$_x$) emissions from motor vehicles.

BACKGROUND AND SUMMARY

A variety of emissions, such as nitrogen oxides (e.g., NO and NO$_2$), are emitted in exhaust gases of internal combustion engines. In order to decrease emissions from motor vehicles, emissions are regulated via use of exhaust system components, such as catalytic converters. Additionally, various gas sensors, including NO$_x$ sensors, are employed to detect the emissions in exhaust gases.

During operation, accurate measurement of NO$_x$ in the exhaust gases may depend on temperature control of a NO$_x$ sensor. U.S. Pat. No. 6,228,252 describes a method to correct NO$_x$ concentration measurement of a NO$_x$ sensor via temperature detection of the sensor. In the cited reference, temperature detection of the NO$_x$ sensor is implemented by measuring internal resistance of a gas concentration measurement cell, as internal resistance is temperature dependent. Depending on a measured offset of the NO$_x$ sensor temperature from a target temperature, the NO$_x$ concentration measurement may be adjusted. An offset from the target temperature of the sensor may occur, for example, due to a sudden change in the temperature of the exhaust gases. Thus, temperature of a NOx sensor may be detected and, in the event of an offset, the NO$_x$ measurement may be corrected without additional temperature sensing components.

In the event of cold start of a motor vehicle, a NO$_x$ sensor operates accurately after it warms-up and reaches an activation temperature, sometimes referred to as a light-off temperature, before it can accurately measure the amount of NO$_x$ contained in the emissions. During the warm-up period, which can have a duration of up to several hundred seconds, the NO$_x$ concentration measurements may be affected by an initial (e.g., ambient) temperature of the sensor causing an erroneous NO$_x$ reading. As such, the NO$_x$ sensor reading is generally ignored during this time. The above reference, while addressing temperature variation of the sensor during operation, fails to address the ambient temperature detection affect on the sensor during warm-up.

The inventor herein has recognized the above problems and has devised an approach to address them. Thus, a method for adjusting the NO$_x$ measurement of a NO$_x$ sensor in response to the ambient temperature is disclosed. The method comprises adjusting an engine operating condition in response to a NO$_x$ indicative reading of the NO$_x$ sensor, the NO$_x$ indicative reading being compensated for ambient temperature effects on the NOx sensor. In this manner, the effect of ambient temperature on the NO$_x$ readings of a NO$_x$ sensor may be reduced during warm-up of the sensor and it may be possible to obtain accurate NO$_x$ readings during the sensor warm-up.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

DETAILED DESCRIPTION

Figure 1:
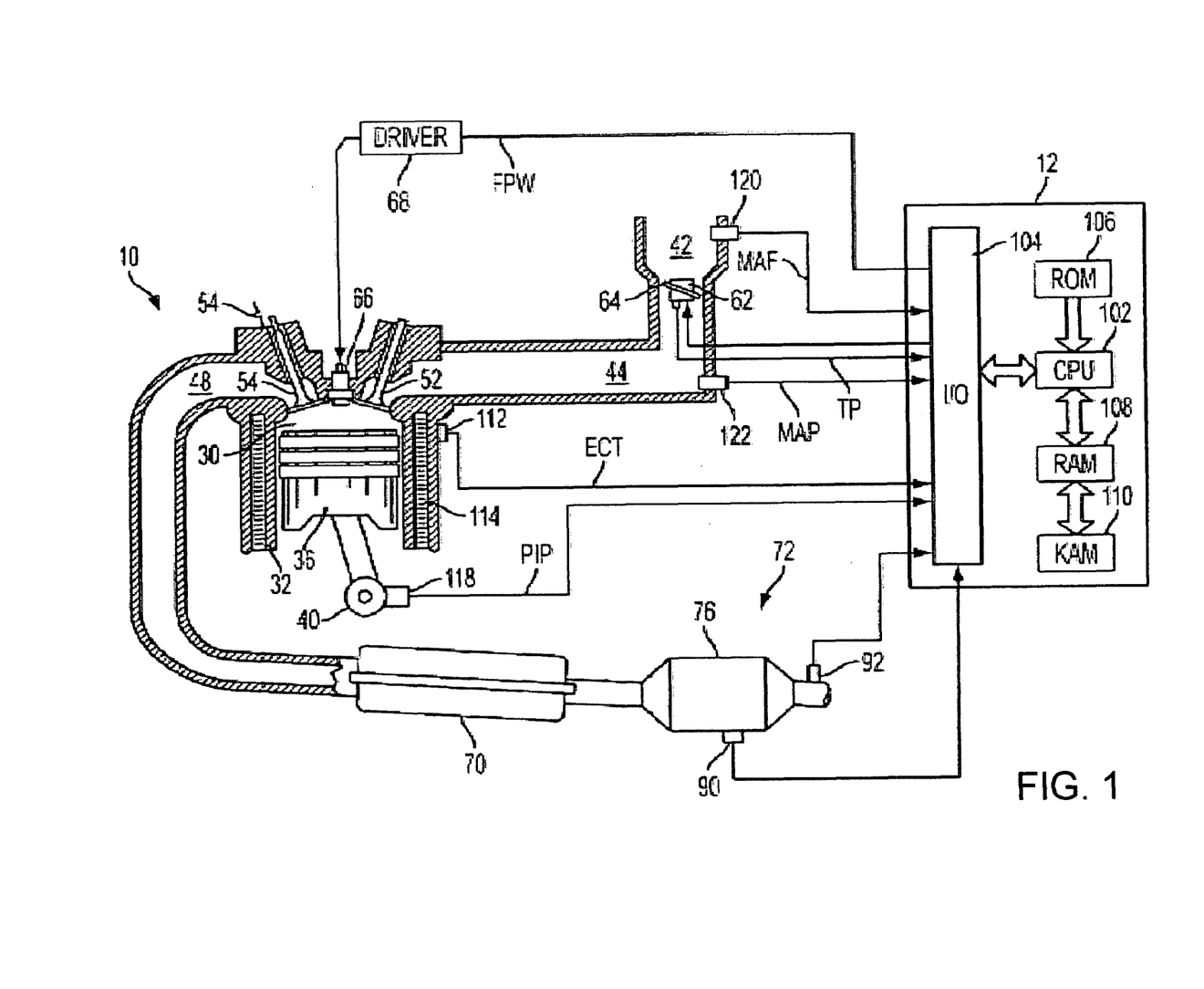
FIG. 1 shows a schematic diagram of an example cylinder of an internal combustion engine including an exhaust system, the exhaust system including a catalyst and a NOx sensor.

Various examples of the approaches described herein may be understood with respect to an example engine and exhaust system including a catalyst and a NO$_x$ sensor, such as that described in FIG. 1. Specifically, FIG. 1 shows an example internal combustion engine 10 comprising a plurality of combustion chambers, only one of which is shown. The engine 10 may be controlled by electronic engine controller 12. In one example, engine 10 may be a common rail direct injection diesel engine.

Combustion chamber 30 of engine 10 includes combustion chamber walls 32 with piston 36 positioned therein and connected to crankshaft 40. Combustion chamber 30 is shown communicating with intake manifold 44 and exhaust manifold 48 via intake valve 52 and exhaust valve 54. While this example shows a single intake and exhaust valve, one or more cylinders may include a plurality of intake and/or exhaust valves.

Fuel injector 66 is shown directly coupled to combustion chamber 30 for delivering liquid fuel directly therein in proportion to the pulse width of signal FPW received from controller 12 via electronic driver 68. Fuel may be delivered by a fuel system (not shown) including a fuel tank, fuel pumps, and a common fuel rail (not shown). In some embodiments, engine 10 may include a plurality of combustion chambers each having a plurality of intake and/or exhaust valves.

Intake manifold 44 may include a throttle body 42 and may include a throttle 62 having a throttle plate 64. In this particular example, the position of throttle plate 64 may be varied by controller 12 via a signal provided to an electric motor or actuator included with throttle 62, a configuration that is commonly referred to as electronic throttle control (ETC). In this manner, throttle 62 may be operated to vary the intake air provided to combustion chamber 30 among other engine cylinders. The position of throttle plate 64 may be provided to controller 12 by throttle position signal TP. Intake manifold 42 may also include a mass air flow sensor 120 and a manifold air pressure sensor 122 for providing respective signals MAF and MAP to controller 12.

Catalytic converter 70 is shown in communication with exhaust manifold 48. In some embodiments, catalytic converter 70 may be a lean NO$_x$ trap (LNT) which may include various precious metals, such as rhodium (Rh). An emission control system 72 is shown downstream of catalytic converter 70. Emission control system 72 may include emission control device 76, which in one example may be a diesel particulate filter (DPF). The DPF may operate actively or passively, and the filtering medium can be of various types of material and geometric construction. One example construction includes a wall-flow ceramic monolith comprising alternating channels that are plugged at opposite ends, thus forcing the exhaust flow through the common wall of the adjacent channels whereupon the particulate matter is deposited.

While this example shows the LNT upstream of a DPF, the DPF may also be positioned upstream of the LNT.

Although the LNT and DPF are normally viewed as separate entities, it is possible to combine the two on one substrate, e.g., a wall-flow ceramic DPF element coated with $NO_x$ storage agents and platinum group metals.

To provide more accurate control of engine operation and/or exhaust air-fuel ratio, one or more exhaust sensors may be used in the exhaust system, such as indicated at 90. Further, various additional exhaust sensors may also be used in emission control system 72, such as various $NO_x$ sensors, ammonia sensors, etc., denoted at 92.

System 72 may also include a reductant injector, such as a fuel injector, located in the engine exhaust (not shown). Further, the system may include a reformer to process fuel into $H_2$, CO, cracked and partially oxidized HCs for injection into the exhaust thereby enabling improved reduction performance. Still other methods of reductant delivery to the exhaust, such as rich combustion, may also be used.

Controller 12 is shown in FIG. 1 as a microcomputer including: microprocessor unit 102, input/output ports 104, an electronic storage medium of executing programs and calibration values, shown as read-only memory (ROM) chip 106 in this particular example, random access memory (RAM) 108, keep alive memory (KAM) 110, and a data bus (I/O). Controller 12 may include instructions, such as code, stored on computer readable medium that can be executed by the controller. Controller 12 is also shown receiving various signals from sensors coupled to engine 10, in addition to those signals previously discussed, including: engine coolant temperature (ECT) from temperature sensor 112 coupled to cooling sleeve 114; a profile ignition pickup signal (PIP) from Hall effect sensor 118 coupled to crankshaft 40 giving an indication of engine speed (RPM); throttle position TP from throttle position sensor 120; and absolute Manifold Pressure Signal MAP from sensor 122.

Combustion in engine 10 can be of various types, depending on operating conditions. While FIG. 1 depicts a compression ignition engine, it will be appreciated that the embodiments described herein may be used in any suitable engine, including but not limited to, diesel and gasoline compression ignition engines, spark ignition engines, direct or port injection engines, etc. Further, various fuels and/or fuel mixtures such as diesel, bio-diesel, etc. may be used.

Figure 2:
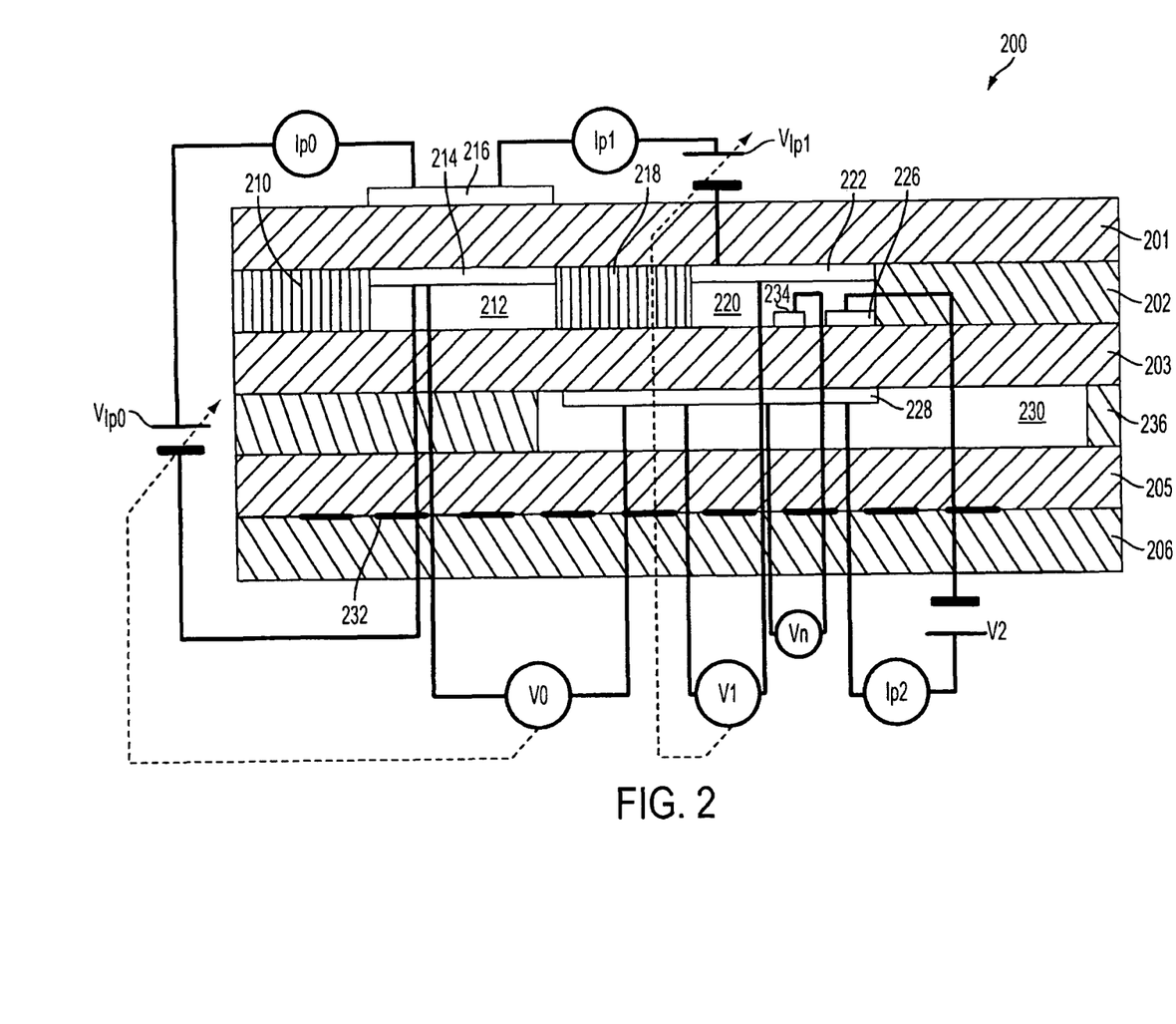
FIG. 2 shows a schematic diagram of an example NO$_x$ sensor.

FIG. 2 shows a schematic view of an example embodiment of a $NO_x$ sensor 200 configured to measure a concentration of $NO_x$ gases in an emissions stream. Sensor 200 may operate as the $NO_x$ sensor 90 or 92 of FIG. 1, for example. Sensor 200 comprises a plurality of layers of one or more ceramic materials arranged in a stacked configuration. In the embodiment of FIG. 2, six ceramic layers are depicted as layers 201, 202, 203, 204, 205, and 206. These layers include one or more layers of a solid electrolyte capable of conducting ionic oxygen. Examples of suitable solid electrolytes include, but are not limited to, zirconium oxide-based materials. Further, in some embodiments, a heater 232 may be disposed between the various layers (or otherwise in thermal communication with the layers) to increase the ionic conductivity of the layers. While the depicted $NO_x$ sensor is formed from six ceramic layers, it will be appreciated that the $NO_x$ sensor may include any other suitable number of ceramic layers.

Layer 202 includes a material or materials creating a first diffusion path 210. First diffusion path 210 is configured to introduce exhaust gases into a first internal cavity 212 via diffusion. A first pair of pumping electrodes 214 and 216 is disposed in communication with internal cavity 212, and is configured to electrochemically pump a selected exhaust gas constituent from internal cavity 212 through layer 201 and out of sensor 200. Generally, the species pumped from internal cavity 212 out of sensor 200 may be a species that may interfere with the measurement of a desired analyte. For example, molecular oxygen (e.g., $O_2$) can potentially interfere with the measurement of $NO_x$ in a $NO_x$ sensor, as oxygen is dissociated and pumped at a lower potential than NOx. Therefore, first pumping electrodes 214 and 216 may be used to remove molecular oxygen from within internal cavity 212 to decrease the concentration of oxygen within the sensor relative to a concentration of $NO_x$ within the sensor.

First diffusion path 210 may be configured to allow one or more components of exhaust gases, including but not limited to the analyte and interfering component, to diffuse into internal cavity 212 at a more limiting rate than the interfering component can be electrochemically pumped out by first pumping electrodes pair 214 and 216. In this manner, almost all of oxygen may be removed from first internal cavity 212 to reduce interfering effects caused by oxygen. Herein, the first pumping electrodes pair 214 and 216 may be referred to as an $O_2$ pumping cell.

The process of electrochemically pumping the oxygen out of first internal cavity 212 includes applying an electric potential $V_{Ip0}$ across first pumping electrode pair 214, 216 that is sufficient to dissociate molecular oxygen, but not sufficient to dissociate $NO_x$. With the selection of a material having a suitably low rate of oxygen diffusion for first diffusion path 210, the ionic current $I_{p0}$ between first pumping electrode pair 214, 216 may be limited by the rate at which the gas can diffuse into the chamber, which is proportional to the concentration of oxygen in the exhaust gas, rather than by the pumping rate of the $O_2$ pumping cell. This may allow a substantial majority of oxygen to be pumped from first internal cavity 212 while leaving $NO_x$ gases in first internal cavity 212. A voltage $V_0$ across first pumping electrode 214 and reference electrode 228 may be monitored to provide feedback control for the application of the electric potential $V_{Ip0}$ across first pumping electrode pair 214, 216.

Sensor 200 further includes a second internal cavity 220 separated from the first internal cavity by a second diffusion path 218. Second diffusion path 218 is configured to allow exhaust gases to diffuse from first internal cavity 212 into second internal cavity 220. A second pumping electrode 222 optionally may be provided in communication with second internal cavity 220. Second pumping electrode 222 may, in conjunction with electrode 216, be set at an appropriate potential $V_{Ip1}$ to remove additional residual oxygen from second internal cavity 220. Second pumping electrode 222 and electrode 216 may be referred to herein as a second pumping electrode pair or a residual $O_2$ monitoring cell. Alternatively, second pumping electrode 222 may be configured to maintain a substantially constant concentration of oxygen within second internal cavity 220. In some embodiments, ($V_{Ip0}$) may be approximately equal to ($V_{Ip1}$) while in other embodiments ($V_{Ip0}$) and ($V_{Ip1}$) may be different. While the depicted embodiment utilizes electrode 216 to pump oxygen from first internal cavity 212 and from second internal cavity 220, it will be appreciated that a separate electrode (not shown) may be used in conjunction with electrode 222 to form an alternate pumping electrode pair to pump oxygen from second internal cavity 220. A voltage $V_1$ across second pumping electrode 222 and reference electrode 228 may be monitored to provide feedback control for the application of the electric potential $V_{Ip1}$ across second pumping electrode pair 222, 216.

First pumping electrode 212 and second pumping electrode 222 may be made of various suitable materials. In some embodiments, first pumping electrode 212 and second pumping electrode may be at least partially made of a material that catalyzes the dissociation of molecular oxygen to the substantial exclusion of $NO_x$. Examples of such materials include, but are not limited to, electrodes containing platinum and/or gold.

Sensor 200 further includes a measuring electrode 226 and a reference electrode 228. Measuring electrode 226 and reference electrode 228 may be referred to herein as a measuring electrode pair. Reference electrode 228 is disposed at least partially within or otherwise exposed to a reference duct 230. In one embodiment, reference duct 230 may be open to the atmosphere and may be referred to as a reference air duct. In another embodiment, reference duct 230 may be isolated by a layer 236 from the atmosphere such that oxygen pumped from second internal cavity 220 may be accumulated within the duct, thus reference duct 230 may be referred to as an oxygen duct.

Measuring electrode 226 may be set at a sufficient potential relative to reference electrode 228 to pump $NO_x$ out of second internal cavity 220. Further, measuring electrode 226 may be at least partially made of a material that catalyzes dissociation or reduction of any $NO_x$. For example, measuring electrode 226 may be made at least partially from platinum and/or rhodium. As $NO_x$ is reduced to $N_2$, the oxygen ions generated are electrochemically pumped from second internal cavity 220. The sensor output is based upon the pumping current flowing through measuring electrode 226 and reference electrode 228, which is proportional to the concentration of $NO_x$ in second internal cavity 220. Thus, the pair of electrodes 226 and 228 may be referred to herein as a $NO_x$ pumping cell.

Sensor 200 further includes a calibration electrode 234. Calibration electrode 234 is used to measure the residual oxygen concentration in second internal cavity 220 according to a Nernst voltage ($V_n$) with reference to reference electrode 228. Thus, calibration electrode 234 and reference electrode 228 may be referred to herein as a calibration electrode pair or as a residual $O_2$ monitoring cell. As shown in FIG. 2, calibration electrode 234 is disposed on the same solid electrolyte layer 203 as measuring electrode 226. Typically, calibration electrode 234 is disposed spatially adjacent to measuring electrode 226. The term "spatially adjacent" as used herein refers to the calibration electrode 234 being in the same volume of space (for example, second internal cavity 220) as measuring electrode 226. Furthermore, placing the calibration electrode 234 in close proximity to measuring electrode 226 may reduce the magnitude of any differences in oxygen concentration at the measuring electrode and at the calibration electrode due to an oxygen concentration gradient between the two electrodes. This may allow residual oxygen concentrations to be measured more accurately. Alternatively, calibration electrode 234 and measuring electrode 226 may be disposed on different solid electrolyte layers. For example, calibration electrode 234 may be disposed on solid electrolyte layer 201 instead of layer 203.

It will be appreciated that the depicted calibration electrode locations and configurations are merely exemplary, and that calibration electrode 234 may have various suitable locations and configurations that allows a measurement of residual oxygen to be obtained. Further, while the depicted embodiment utilizes electrode 228 as a reference electrode of the calibration electrode pair, it will be appreciated that a separate electrode (not shown) may be used in conjunction with calibration electrode 234 to form an alternative calibration electrode pair configuration.

It should be appreciated that the $NO_x$ sensors described herein are merely example embodiments of $NO_x$ sensors, and that other embodiments of $NO_x$ sensors may have additional and/or alternative features and/or designs. For example, in some embodiments, a NOx sensor may include only one diffusion path and one internal cavity, thereby placing the first pumping electrode and measuring electrode in the same internal cavity. In such an embodiment, a calibration electrode may be disposed adjacent to the measuring electrode so that the residual oxygen concentration of an exhaust gas at or near the measuring electrode can be determined with a minimized impact from any oxygen concentration gradient.

Upon cold start of a motor vehicle, engine components, such as $NO_x$ sensors, may not provide accurate readings until they warm-up to certain operating temperatures in order to run effectively and/or efficiently. Depending on the vehicle soak time (e.g., a duration during which the engine and/or vehicle has been in a shut-down condition), at key-on under cold start conditions, the temperature of a $NO_x$ sensor may be equal to the temperature of the air surrounding the vehicle (e.g., the external air temperature). The ambient temperature (e.g., initial temperature) of the sensor is low with respect to its operating temperature; thus, $NO_x$ readings obtained during warm-up of the sensor, which can have a duration of up to several hundred seconds, may be erroneous. The flowcharts of FIGS. 3-5, which are described in detail below, depict procedures for operating a NOx sensor in temperature sensing and $NO_x$ sensing modes and, more specifically, for determining the ambient temperature of the $NO_x$ sensor and utilizing the ambient temperature measurement to correct $NO_x$ readings during the warm-up operation.

Figure 3:
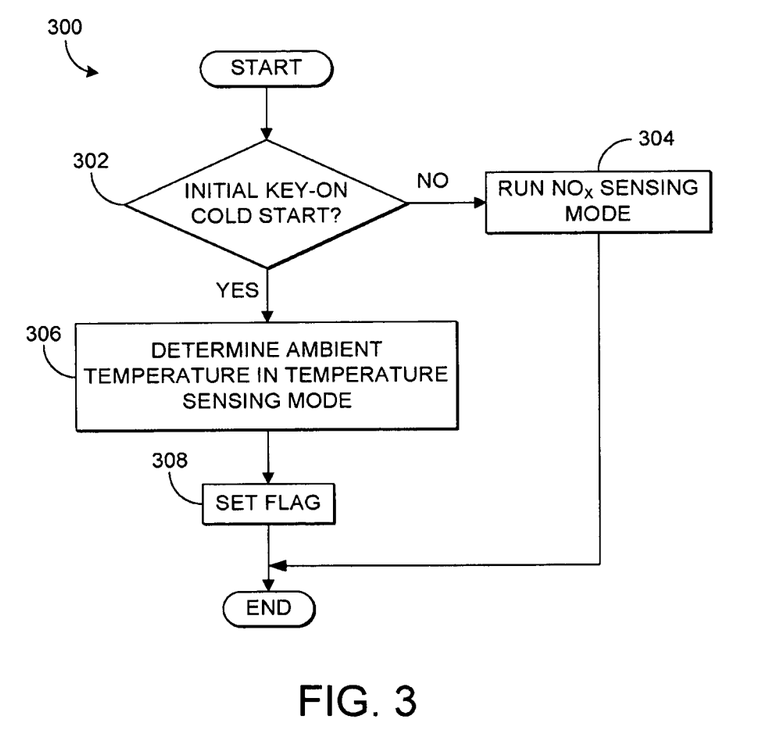
FIG. 3 shows a flow chart illustrating an example start-up routine of a NO$_x$ sensor.

FIG. 3 shows a flow chart illustrating an exemplary start-up routine 300 for a $NO_x$ sensor, such as sensor 200 of FIG. 2. Specifically, the routine determines if the $NO_x$ sensor is under cold start conditions and accordingly selects the mode of operation for the sensor. In this manner, the control system allows the $NO_x$ sensor to function in an appropriate mode of operation.

At 302, it is determined if an initial key-on of a motor vehicle has occurred and if the vehicle is under cold start conditions. Cold start conditions imply the operational components of the engine are not warmed-up to working temperature (e.g., the vehicle has been shut-down for greater than a minimum duration such that its components have cooled to ambient temperatures. In one example, depending on the soak time of the vehicle, the exhaust and/or NOx sensor may still be hot and, thus, the reading from the $NO_x$ sensor would not be the ambient temperature. As such, if it is not a cold start, and thus the $NO_x$ sensor is warmed-up, the sensor may be run in $NO_x$ sensing mode at 304.

In a situation in which the vehicle is under cold start conditions, the $NO_x$ sensor 200 is run in temperature sensing mode. By running the $NO_x$ sensor in temperature sensing mode before the sensor has warmed-up to its operating temperature, and in some cases before the sensor experiences exhaust gas from a first combustion event of the engine from rest, an accurate measurement of the ambient temperature may be generated, thus enabling accurate measurement of the $NO_x$ concentration during warm-up.

After key-on and before a first combustion of the engine, an ambient temperature of the $NO_x$ sensor 200 is determined at 306 of routine 300, as described in greater detail below. Once the ambient temperature is determined, a flag is set to indicate the temperature sensing mode is complete at 308.

Figure 4:
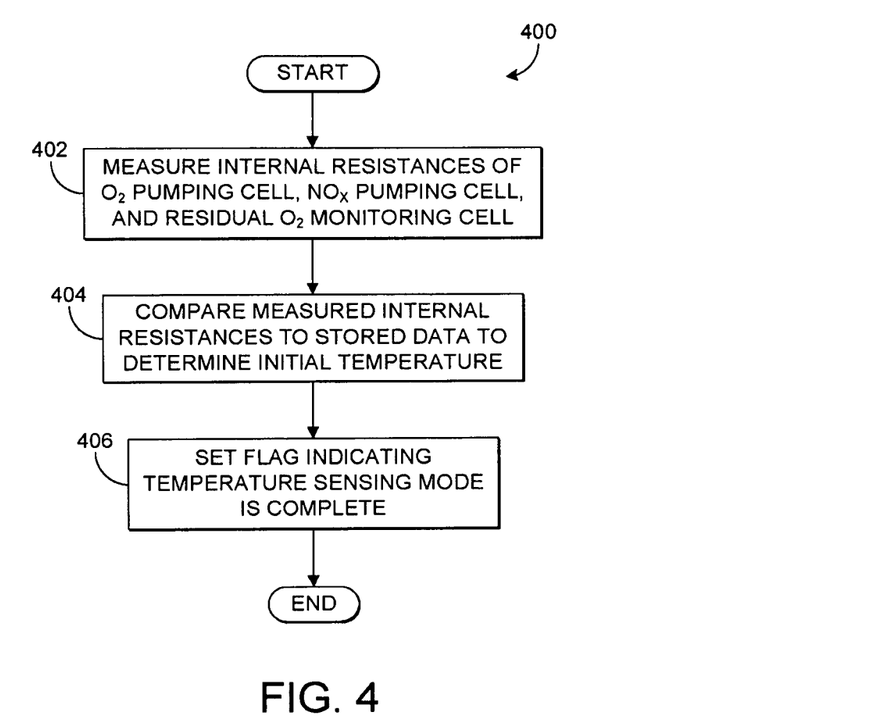
FIG. 4 shows a flow chart illustrating a temperature sensing mode of a NO$_x$ sensor.

Further details of the temperature sensing mode routine 400 of the $NO_x$ sensor are illustrated in the flow chart of FIG. 4. It should be understood that the temperature sensing mode procedure 400 is performed, in one example, after key-on and before the first combustion of the engine. In this manner, the ambient temperature of the $NO_x$ sensor may be measured accurately without an influence of variables such as exhaust gas temperature. One method in which the ambient temperature of the sensor may be identified is by measuring at 402 the internal resistances of the $O_2$ pumping cell, the $NO_x$ pumping cell, and the residual $O_2$ monitoring cell. The internal resistance of a cell is dependent on the temperature of the cell, thus, the internal resistance of the cell changes with a change in temperature. For example, as the temperature increases, the internal resistance decreases.

There are a variety of methods for detecting the internal resistance of a set of electrodes. The following examples will be described with reference to the $O_2$ pumping cell; however, the methods may apply to any of the aforementioned cells. One method for determining the internal resistance of the $O_2$ pumping cell is the voltage drop method. According to the voltage drop method, a constant current is applied across electrodes 214 and 216 for an amount of time ranging from one tenth of a microsecond to tens of seconds. As the constant current is applied, an instantaneous voltage change is measured. A second method for determining the internal resistance of the $O_2$ pumping cell is the transient current method. In contrast to the voltage drop method, the transient current method entails applying a constant voltage across electrodes 214 and 216 for an amount of time ranging from one tenth of a microsecond to tens of seconds. As the constant voltage is applied, an instantaneous current change is measured.

At 404 of procedure 400 in FIG. 4, data obtained from one of the abovedescribed methods for measuring the internal resistance of the cell is compared to data stored in the $NO_x$ controller to determine the initial temperature of the cell. Once the ambient temperature is determined, a flag is set indicating that the temperature sensing mode of the $NO_x$ sensor is complete at 406.

Turning back to FIG. 3, if it is determined at 302 that it is not a vehicle cold start, the $NO_x$ sensor is run in $NO_x$ sensing mode. Details of an example $NO_x$ sensing mode routine 500 are depicted in the flow chart of FIG. 5. Specifically, the routine allows the controller to determine the $NO_x$ concentration in the exhaust gases and accordingly make corrections to the $NO_x$ readings based on the temperature of the sensor.

Figure 5:
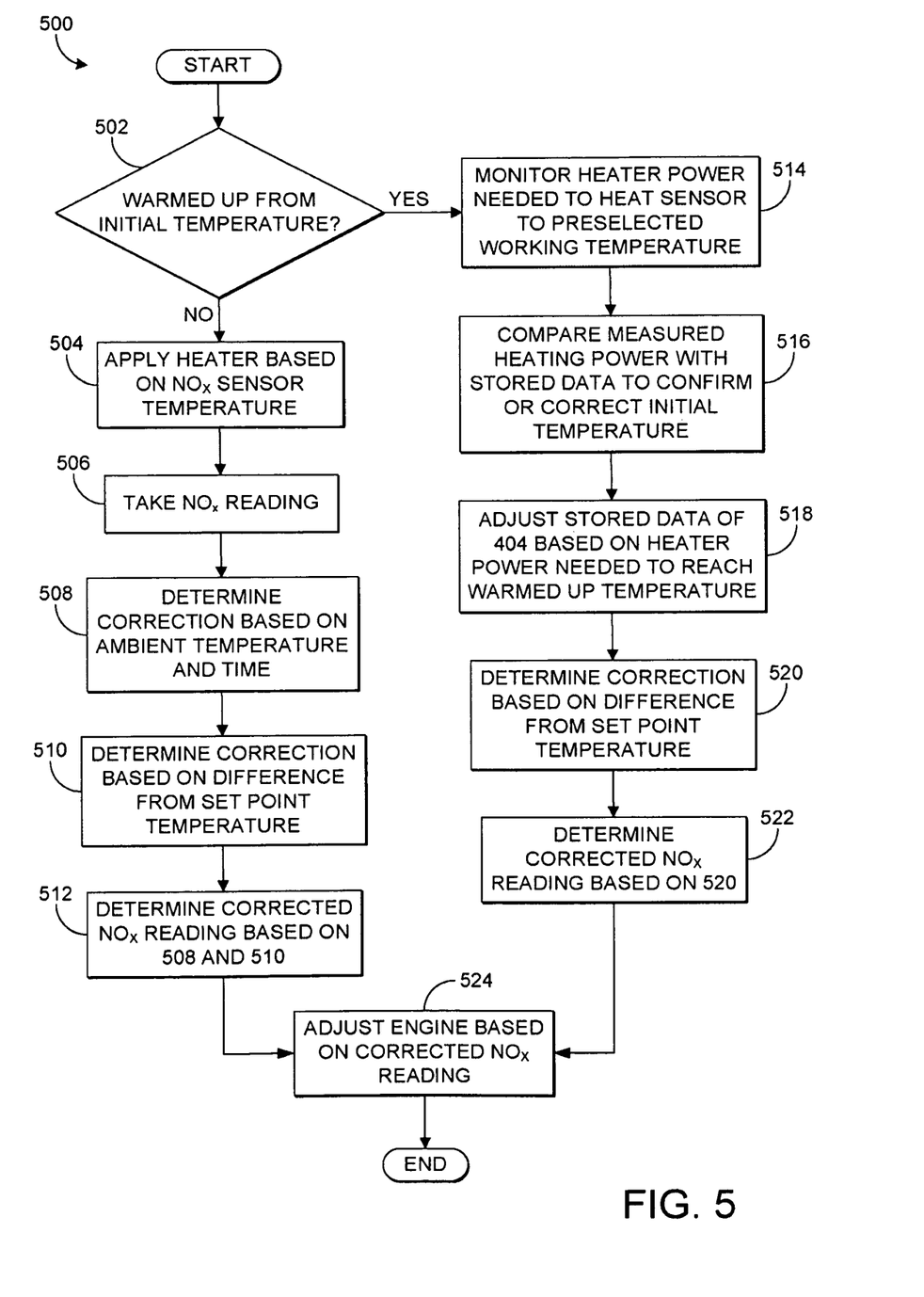
FIG. 5 shows a flow chart illustrating a NO$_x$ sensing mode of a NO$_x$ sensor.

At 502, it is determined if the NOx sensor has warmed-up to its set-point temperature (e.g., activation temperature) from its initial temperature. If the NOx sensor has not warmed-up to its activation temperature, the heater may be activated and applied with an intensity and duration dependent on the current temperature of the $NO_x$ sensor. With the application of the heater, the $NO_x$ sensor may reach its operating temperature faster than relying on only the heat from the exhaust gases.

As the $NO_x$ sensor is warmed-up by transient exhaust gas and/or the heater, a concentration of $NO_x$ in the exhaust gases may be measured at 506 of routine 500. Due to a sensor temperature that is less than the activation temperature of the $NO_x$ sensor, the $NO_x$-indicative reading may need to be compensated (e.g., corrected). A correction to the $NO_x$ reading may be based on one or more factors involving the temperature of the sensor, as described herein.

Figure 6:
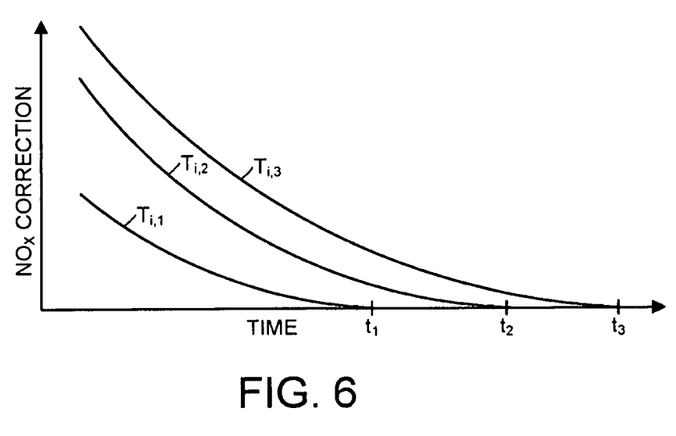
FIG. 6 shows an example map illustrating NO$_x$ corrections based on time and temperature of the sensor.

At 508, a correction to the $NO_x$ sensor reading is determined based on the ambient temperature (e.g., from 306) and the time from start up, or key on, of the sensor. An example of this correction is illustrated by the map in FIG. 6. The map shows the $NO_x$ correction based on time from start up for three different ambient temperatures, $T_{i,1}$, $T_{i,2}$, and $T_{i,3}$, where $T_{i,1} > T_{i,2} > T_{i,3}$. As can be seen in FIG. 6, the higher the ambient temperature, the faster the $NO_x$ sensor reaches its activation temperature ($t_1$, $t_2$, and $t_3$ for temperatures $T_{i,1}$, $T_{i,2}$, and $T_{i,3}$, respectively) and the smaller the $NO_x$ correction during warm-up.

A second correction to the $NO_x$-indicative measurement may be determined at 510 of routine 500 in FIG. 5. The second correction is based on a difference of the sensor temperature from a set-point temperature (e.g., a desired operating temperature set-point). During operation of a $NO_x$ sensor, the temperature may be monitored to ensure it is close to its activation temperature, for example, the temperature of the sensor may change due to factors such as variations in exhaust gas temperatures, flow rate, heater operation, etc. The instantaneous temperature of the sensor may be identified via one of the methods described above for measuring the internal resistance of the sensor. In this case, however, the correction to the $NO_x$ reading is independent of the ambient temperature of the $NO_x$ sensor.

At 512, the corrected $NO_x$ concentration measurement is determined based on the corrections due to the ambient temperature (from 508) and the deviation of the instantaneous temperature (from 510) from the set-point temperature of the sensor.

According to routine 500 of FIG. 5, a different procedure is carried out if it is determined the $NO_x$ sensor has warmed-up from the ambient temperature at 502. If the $NO_x$ sensor has already reached its activation temperature, a correction due to the ambient temperature may no longer be included and routine 500 proceeds to 514.

At 514, the heater power required to heat the sensor to a preselected working temperature (e.g., activation temperature) is monitored. The amount of power to heat the sensor to a desired temperature from ambient conditions may also be used to determine the initial (ambient) temperature of the sensor—although the information is available after the warm-up of the sensor is complete. Therefore, the measured heating power may be compared with stored data to confirm or correct the measured value of the initial temperature at 516. The stored data of step 404 of routine 400 in FIG. 4 may then be corrected based on the power measured to heat the sensor to its activation temperature at 518.

At 520 of routine 500 in FIG. 5, a correction to the $NO_x$ concentration reading is determined based on a difference of the temperature of the sensor from a set point temperature (e.g., activation temperature). As described earlier, once a $NO_x$ sensor reaches its activation temperature, the temperature of the sensor may fluctuate due to factors such as changes in the temperature of the exhaust gases. Thus, the instantaneous temperature of the sensor may be measured periodically, via measurement of the internal resistance of the sensor as described above, to ensure the $NO_x$ concentration reading is accurate.

If a difference in temperature from the activation temperature is measured at 520, the corrected $NO_x$ reading is determined at 522. Depending on the instantaneous temperature of the sensor, the $NO_x$ reading may or may not be adjusted.

Once corrections to the $NO_x$ reading have been determined at 512 and 522 of routine 500 in FIG. 5, the engine operation may be adjusted responsive to the corrected $NO_x$ reading. For example, in some embodiments, if the corrected $NO_x$ reading demonstrates there is a high concentration of $NO_x$ in the emissions, a signal may be sent to start $NO_x$ trap regeneration. In other embodiments, if the corrected $NO_x$ reading is too high, a signal may be sent to the vehicle operator or a diagnostic code set indicating there may be degradation in the exhaust system.

Thus, by the actions described above, it is possible to obtain exhaust NOx information during a greater range of operation, while providing appropriate temperature corrections. Specifically, in one example, the actions include during warm-up of the NOx sensor and during cold engine starting: adjusting an engine operating condition in response to a NOx-indicative reading of the NOx sensor, the NOx-indicative reading being compensated based on an ambient temperature of the NOx sensor, the ambient temperature identified by the NOx sensor; and after warm-up of the NOx sensor: adjusting an engine operating condition in response to a NOx-indicative reading of the NOx sensor, the NOx-indicative reading being compensated based on a deviation of NOx sensor temperature from a set-point temperature.

Note that the example control and estimation routines included herein can be used with various engine and/or vehicle system configurations. The specific routines described herein may represent one or more of any number of processing strategies such as event-driven, interrupt-driven, multi-tasking, multi-threading, and the like. As such, various acts, operations, or functions illustrated may be performed in the sequence illustrated, in parallel, or in some cases omitted. Likewise, the order of processing is not necessarily required to achieve the features and advantages of the example embodiments described herein, but is provided for ease of illustration and description. One or more of the illustrated acts or functions may be repeatedly performed depending on the particular strategy being used. Further, the described acts may graphically represent instructions to be programmed into the computer readable storage medium in the engine control system.

It will be appreciated that the configurations and routines disclosed herein are exemplary in nature, and that these specific embodiments are not to be considered in a limiting sense, because numerous variations are possible. For example, the above technology can be applied to V-6, I-4, I-6, V-12, opposed 4, and other engine types. The subject matter of the present disclosure includes all novel and nonobvious combinations and subcombinations of the various systems and configurations, and other features, functions, and/or properties disclosed herein.

The following claims particularly point out certain combinations and subcombinations regarded as novel and nonobvious. These claims may refer to "an" element or "a first" element or the equivalent thereof. Such claims should be understood to include incorporation of one or more such elements, neither requiring nor excluding two or more such elements. Other combinations and subcombinations of the disclosed features, functions, elements, and/or properties may be claimed through amendment of the present claims or through presentation of new claims in this or a related application.

Such claims, whether broader, narrower, equal, or different in scope to the original claims, also are regarded as included within the subject matter of the present disclosure.

The invention claimed is:

1. A method of controlling an engine $NO_x$ sensor coupled in an engine exhaust, comprising:
during warm-up of the $NO_x$ sensor and during cold engine starting: adjusting an engine operating condition in response to a $NO_x$-indicative reading of the $NO_x$ sensor, the $NO_x$-indicative reading being compensated based on an ambient temperature identified by the $NO_x$ sensor before exhaust from a first combustion event of the engine from rest reaches the $NO_x$ sensor.

2. The method of claim 1 wherein the $NO_x$ sensor is operated in at least two modes, a first mode including operating the $NO_x$ sensor to generate the $NO_x$-indicative reading, and a second mode including operating the $NO_x$ sensor to generate the ambient temperature.

3. The method of claim 2 further comprising operating the $NO_x$ sensor in the second mode in response to a key-on.

4. The method of claim 3 further comprising operating the $NO_x$ sensor in the second mode before exhaust gas from the first combustion event from engine rest reaches the $NO_x$ sensor.

5. The method of claim 2 wherein, during the engine cold start, the $NO_x$ sensor first operates in the second mode, and then operates in the first mode, where the $NO_x$-indicative reading is compensated responsive to the generated ambient temperature, the engine adjusted responsive to the compensated $NO_x$-indicative reading even before the $NO_x$ sensor reaches a warmed-up operating temperature.

6. The method of claim 2 wherein the compensation of the $NO_x$-indicative reading further includes compensating the reading based on a time since engine start.

7. The method of claim 2 wherein the $NO_x$ sensor includes a heater, and where the $NO_x$ sensor operates in the second mode before even a first activation of the heater from the engine start.

8. The method of claim 2 wherein the $NO_x$ sensor includes a plurality of pumping cells.

9. The method of claim 8 wherein generating the ambient temperature in the second mode includes detecting an internal resistance of the pumping cells.

10. A system, comprising:
an engine exhaust;
a $NO_x$ sensor coupled in the engine exhaust, the $NO_x$ sensor having a heater; and
a control system including a computer readable storage medium, the medium including instructions thereon, the control system receiving communication from the $NO_x$ sensor, the medium comprising:
instructions for, during warm-up of the $NO_x$ sensor and before exhaust from a first combustion event of the engine from rest reaches the $NO_x$ sensor, and before the heater is activated, identifying a first ambient temperature based on the $NO_x$ sensor communication;
instructions for, during engine starting and before the $NO_x$ sensor reaches a warmed-up operating temperature and after the first ambient temperature is identified, identifying an exhaust $NO_x$ amount based on the $NO_x$ sensor;
instructions for compensating the exhaust $NO_x$ amount for the first ambient temperature; and
instructions for adjusting an engine operating condition in response to the compensated exhaust $NO_x$ amount.

11. The system of claim 10 further comprising instructions for activating and maintaining the heater until the $NO_x$ sensor reaches a set-point temperature.

12. The system of claim 11 further comprising instructions for identifying a second ambient temperature based on an amount of power used to heat the $NO_x$ sensor to the set-point temperature.

13. The system of claim 12 further comprising instructions for adjusting identification of the first ambient temperature of the $NO_x$ sensor based on the identification of the second ambient temperature.

14. The system of claim 13 further comprising instructions for adjusting the heater to maintain the set-point temperature.

15. The system of claim 14 further comprising instructions for, after the $NO_x$ sensor has warmed-up to its set-point temperature, identifying a current temperature of the $NO_x$ sensor.

16. The system of claim 15 further comprising instructions for, after the current temperature is identified, identifying the exhaust $NO_x$ amount based on the $NO_x$ sensor, the exhaust $NO_x$ amount compensated for the current temperature.

17. The system of claim 16 further comprising instructions for adjusting an engine operating condition in response to the compensated exhaust $NO_x$ amount.

18. A method of controlling an engine of a vehicle during engine operation, the engine having an exhaust, and a $NO_x$ sensor having a heater coupled in the exhaust, the method comprising:

during warm-up of the $NO_x$ sensor, during cold engine starting, before the heater is activated and before exhaust from a first combustion event of the engine from rest reaches the $NO_x$ sensor: adjusting an engine operating condition in response to a $NO_x$-indicative reading of the $NO_x$ sensor, the $NO_x$-indicative reading being compensated based on an ambient temperature of the $NO_x$ sensor, the ambient temperature identified by the $NO_x$ sensor; and after warm-up of the $NO_x$ sensor: adjusting an engine operating condition in response to a $NO_x$-indicative reading of the $NO_x$ sensor, the $NO_x$-indicative reading being compensated based on a deviation of $NO_x$ sensor temperature from a set-point temperature.

19. The method of claim 18 wherein the $NO_x$ sensor is operated in at least two modes, a first mode including operating the $NO_x$ sensor to generate the $NO_x$-indicative reading, and a second mode including operating the $NO_x$ sensor to generate the ambient temperature, where during an engine start that is not a cold engine start, the $NO_x$ sensor is operated in the first mode.

20. The method of claim 19 wherein the $NO_x$ sensor operates in the second mode in response to a key-on, and wherein the $NO_x$ sensor operates in the second mode after warm-up of the $NO_x$ sensor.

* * * * *